US010588640B2

(12) United States Patent
Steinhauser et al.

(10) Patent No.: US 10,588,640 B2
(45) Date of Patent: Mar. 17, 2020

(54) SPACE-SAVING RATCHET UNIT WITH FREEWHEEL

(71) Applicant: Aesculap AG, Tuttlingen (DE)

(72) Inventors: Jan Steinhauser, Sigmaringen (DE); Ralf Pfister, Trossingen (DE)

(73) Assignee: Aesculap AG (DE)

( * ) Notice: Subject to any disclaimer, the term of this patent is extended or adjusted under 35 U.S.C. 154(b) by 119 days.

(21) Appl. No.: 15/744,957

(22) PCT Filed: Jul. 6, 2016

(86) PCT No.: PCT/EP2016/065986
§ 371 (c)(1),
(2) Date: Jan. 15, 2018

(87) PCT Pub. No.: WO2017/012876
PCT Pub. Date: Jan. 26, 2017

(65) Prior Publication Data
US 2018/0206853 A1    Jul. 26, 2018

(30) Foreign Application Priority Data
Jul. 22, 2015   (DE) .................. 10 2015 111 878

(51) Int. Cl.
*A61B 17/16* (2006.01)
*A61B 17/84* (2006.01)
(Continued)

(52) U.S. Cl.
CPC ........ *A61B 17/162* (2013.01); *A61B 17/1624* (2013.01); *A61B 17/84* (2013.01);
(Continued)

(58) Field of Classification Search
CPC ... A61B 17/16; A61B 17/1613; A61B 17/162; A61B 17/1622; A61B 17/1624;
(Continued)

(56) References Cited

U.S. PATENT DOCUMENTS 3,120,845 A    2/1964  Horner
4,487,270 A    12/1984 Huber
(Continued)

FOREIGN PATENT DOCUMENTS

DE    1871193 U    4/1963
DE    1214826 B    4/1966
(Continued)

OTHER PUBLICATIONS

German Search Report for German Application No. 10 2015 111 877.7, with English translation, dated May 11, 2016, 14 Pages.
(Continued)

*Primary Examiner* — Eric S Gibson
(74) *Attorney, Agent, or Firm* — RatnerPrestia

(57) ABSTRACT

A medical device, and a ratchet for a medical device, include a torque-guiding element and a torque discharging element, between which a switchable toothed unit is arranged so that, in accordance with a switching position of the toothed unit, torque from the torque-guiding element is transferred to the torque discharging element, said toothed unit includes two torque transfer sleeves arranged in a nested manner and which are arranged and produced such that both can be brought into torque-transmitting contact with an intermediate sleeve.

11 Claims, 3 Drawing Sheets

Figure 2:
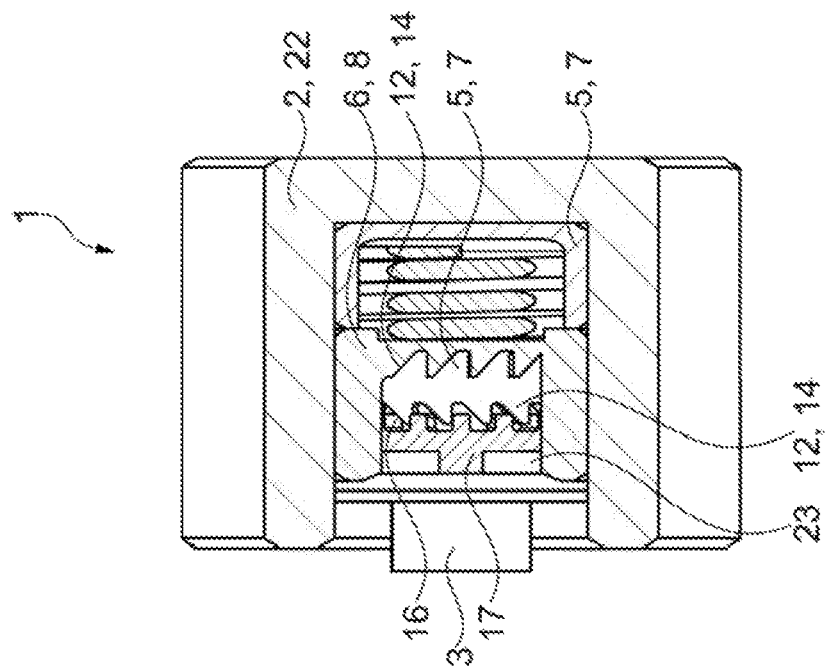

(51) Int. Cl.
B25B 13/46 (2006.01)
B25B 23/14 (2006.01)
A61B 17/00 (2006.01)

(52) U.S. Cl.
CPC .......... B25B 13/466 (2013.01); B25B 23/141 (2013.01); *A61B 2017/00407* (2013.01)

(58) Field of Classification Search
CPC . A61B 17/1626; A61B 17/1628; B25B 13/46; B25B 13/461; B25B 13/466; B25B 23/14; B25B 23/141
See application file for complete search history.

(56) References Cited

U.S. PATENT DOCUMENTS

| | | | |
|---|---|---|---|
| 5,458,206 A * | 10/1995 | Bourner | B25B 23/14 173/104 |
| 5,613,585 A * | 3/1997 | Tiede | B25B 13/463 192/43.1 |
| 5,619,891 A * | 4/1997 | Tiede | B25B 13/463 192/43.1 |
| 5,741,263 A * | 4/1998 | Umber | A61B 17/162 279/75 |
| 5,794,715 A | 8/1998 | Norman | |
| 5,888,200 A * | 3/1999 | Walen | A61B 17/1622 606/167 |
| RE37,905 E | 11/2002 | Bourner et al. | |
| 6,817,458 B1 * | 11/2004 | Gauthier | B25B 13/463 192/43.1 |
| 7,181,997 B1 * | 2/2007 | Rinner | B25B 13/463 81/58.3 |
| 7,926,390 B2 * | 4/2011 | Bennett | A61B 17/1624 81/177.85 |
| 8,597,316 B2 * | 12/2013 | McCombs | A61B 17/162 606/167 |
| 8,786,233 B2 | 7/2014 | Fair et al. | |
| 8,801,713 B2 * | 8/2014 | del Rio | A61B 17/1615 606/80 |
| 8,985,593 B1 | 3/2015 | Gao | |
| 9,113,917 B2 * | 8/2015 | del Rio | A61B 17/1615 |
| 9,381,023 B2 * | 7/2016 | del Rio | A61B 17/1615 |
| 9,681,879 B2 * | 6/2017 | del Rio | A61B 17/1615 |
| 9,937,009 B2 | 4/2018 | Schroeder et al. | |
| 2002/0058958 A1 * | 5/2002 | Walen | A61B 17/1615 606/170 |
| 2002/0151902 A1 * | 10/2002 | Riedel | A61B 17/162 606/80 |
| 2003/0110901 A1 * | 6/2003 | Shiao | B25B 13/468 81/62 |
| 2006/0048610 A1 | 3/2006 | Hu | |
| 2006/0053974 A1 * | 3/2006 | Blust | A61B 17/162 81/3.07 |
| 2006/0248987 A1 * | 11/2006 | White | A61B 17/1624 81/62 |
| 2007/0260257 A1 | 11/2007 | Phan | |
| 2009/0234365 A1 | 9/2009 | Gross | |
| 2010/0063524 A1 * | 3/2010 | McCombs | A61B 17/162 606/167 |
| 2010/0163264 A1 | 7/2010 | Simm et al. | |
| 2011/0061500 A1 | 3/2011 | Huang | |
| 2012/0055296 A1 | 3/2012 | Landowski | |
| 2014/0102741 A1 | 4/2014 | Sekino et al. | |
| 2014/0277203 A1 | 9/2014 | Atoulikian et al. | |
| 2015/0021062 A1 | 1/2015 | Sekino et al. | |
| 2015/0148176 A1 | 5/2015 | Schroeder et al. | |
| 2015/0351777 A1 | 12/2015 | Lizardi et al. | |
| 2015/0367487 A1 | 12/2015 | Nino et al. | |
| 2016/0089154 A1 | 3/2016 | Chien et al. | |
| 2016/0325414 A1 | 11/2016 | Mizuno et al. | |
| 2017/0156813 A1 | 6/2017 | Cutler | |
| 2017/0314711 A1 | 11/2017 | Helstern | |
| 2017/0367748 A1 | 12/2017 | Plotkin | |
| 2018/0104801 A1 | 4/2018 | Bakula et al. | |
| 2018/0206853 A1 * | 7/2018 | Steinhauser | A61B 17/84 |
| 2018/0206856 A1 | 7/2018 | Högerle et al. | |
| 2018/0242982 A1 * | 8/2018 | Laughlin | A61B 17/1631 |
| 2019/0059910 A1 | 2/2019 | Adams et al. | |
| 2019/0125421 A1 * | 5/2019 | Smith | A61B 17/8875 |
| 2019/0231447 A1 * | 8/2019 | Ebbitt | A61B 34/10 |

FOREIGN PATENT DOCUMENTS

| | | |
|---|---|---|
| DE | 4342464 A1 | 6/1995 |
| DE | 19730300 A1 | 9/1998 |
| DE | 29723472 U1 | 9/1998 |
| DE | 19951888 A1 | 5/2000 |
| DE | 19942292 A1 | 10/2000 |
| DE | 102005034114 A1 | 2/2006 |
| DE | 102006057283 A1 | 6/2008 |
| DE | 102007048928 A1 | 4/2009 |
| DE | 102011088252 A1 | 6/2013 |
| EP | 2701879 A1 | 3/2014 |
| WO | 2013020877 A1 | 2/2013 |

OTHER PUBLICATIONS

International Search Report and Written Opinion for International Application No. PCT/EP2016/065988, dated Mar. 21, 2017, 18 pages.
German Search Report for German Application No. 10 2015 111 878.5, with translation, dated May 9, 2016, 11 Pages.
International Search Report and Written Opinion for International Application No. PCT/EP2016/065986, dated Mar. 21, 2017, 12 Pages.
Non Final office Action for U.S. Appl. No. 15/744,960, dated Dec. 9, 2019, 30 pages.

* cited by examiner

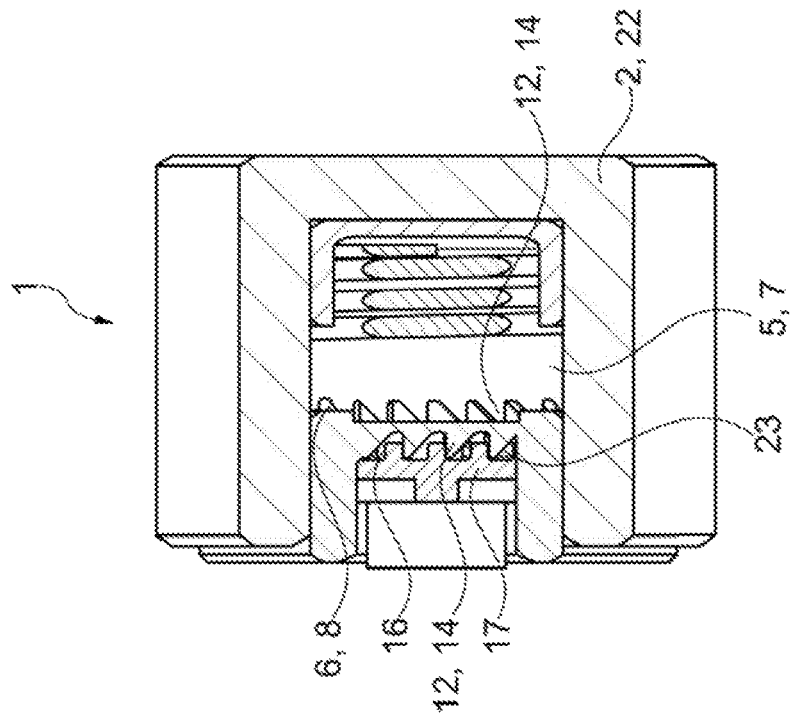
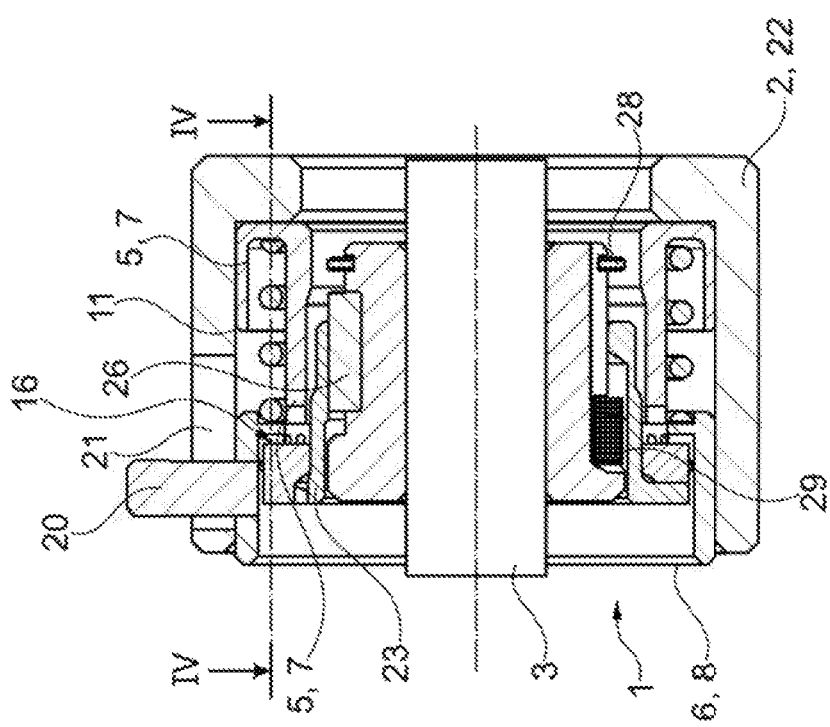

SPACE-SAVING RATCHET UNIT WITH FREEWHEEL

RELATED APPLICATIONS

This application is the United States national phase entry of International Application No. PCT/EP2016/065986, filed Jul. 6, 2016, which is related to and claims the benefit of priority of German Application No. 10 2015 111 878.5, filed Jul. 22, 2015. The contents of International Application No. PCT/EP2016/065986 and German Application No. 10 2015 111 878.5 are incorporated by reference herein in their entireties.

FIELD

The invention relates to a ratchet for a medical device such as a drilling, milling and/or screwing machine for drilling/milling a bone and/or for setting screws in the bone or for screwing an implant, comprising a torque-guiding element and a torque discharging element between which a switchable toothed unit is arranged so that, in accordance with a switching position of the toothed unit, torque from the torque-guiding element is transferred to the torque discharging element in only one sense of rotation which can be selected.

BACKGROUND

DE 10 2011 088 252 A1 discloses an add-on ratchet for driving screwing fools which serve for unscrewing and tightening screw elements and cast be selectively driven in two rotary directions, with the option that the add-on ratchet can be implemented as a straight add-on part and as an angular add-on part as well provided in a sleeve-shaped housing are two dogs at a distance from one another, which are supported such that they can be rotated relative to the housing but are axially fixed. At their end faces facing each other, the dogs have their peripheral region each provided with a ratchet toothing which have an inverse design with respect to each other. Opposite to the respective ratchet toothing of the two dogs, a drive ring is provided on the side facing the respective dog with a corresponding ratchet soothing that can be coupled to it. The drive ring is mounted in the housing so as to be axially shiftable relative to it and is supported on the respective dog by means of spring means. The add-on ratchet further includes a drive tool which can be rotatably put through a polygonal opening of the dog and can be locked in place with its coupling end in a polygonal profile of the drive ring in a torque-proof manner. By means of the drive took the drive ring or the respective drive ring can be axially shifted away from the dog through which the drive tool can be put, namely to a position where it is uncoupled from it and at the same time to a position where it is coupled to the other dog carrying the screwing tool.

This add-on ratchet is intended for conventional socket wrenches. Two rotatably mounted, axially fixed dogs are comprised which are provided with saw toothings. A non-rotatable, axially shiftable drive ring with a two-sided toothing is employed. Shifting the drive ring allows to change between a left-hand and right-hand rotation.

A further ratchet means is also known from DE 297 25 472 U1. This document discloses a ratchet means for operating a socket, e.g. a hexagonal socket, comprising a drive part with provisions for force introduction, a driven part which is concentrically arranged relative to the drive part and has its outer end face provided with a centrally projecting square trunnion for engaging a square opening of a socket, and a ratchet element or dog element between the drive part and the driven part. A special feature highlighted here consists m that two body parts with substantially identical design of its outer shell surface are provided successively in the rotary axis direction, with at least the drive part having a square insertion opening in its end face axially opposite to the driven pin.

A switchable screwdriver ratchet means is disclosed in DE 199 51 888 A1 in a further development of the last-mentioned prior art. This document discloses a switchable ratchet screwdriver which admittedly comprises counter-rotating freewheels axially arranged in series inside a housing, a central tool shaft and a dog portion at the level of the freewheels, which can be selectively shifted to an active position left/right by means of the freewheels. The highlighted special feature consists in that the screwdriver is constructed in the manner of a ball pen comprising a slim, tubular housing, a shaft protruding from the housing at the front and a switching press button projecting from the rear end and acting against a spring force; in addition, a fastening clip is provided on the housing.

However, in the above document as well as in the above-named utility model two freewheels are used which have internal and opposite toothings. A slide shaft having an external toothing is used in addition. An axial movement of the slide shaft allows to change between a left-hand and right-hand rotation.

However, the existing solutions have several deficiencies that have to be rectified. This means that the solutions imply a high axial space requirement and in most cases have a high radial space requirement, too. A convenient change of the operating mode is not possible. Usually, the add-on ratchet has to be turned. Moreover, the existing solutions cannot be efficiently combined with additional switching means, for instance with a freewheel. Even if a freewheel is applied, this is only possible by pushing out the slide shaft. A reintroduction of the latter is generally jerky, however. Furthermore, the arrangement of the freewheels dictates the order of the traversed switching positions in this case.

SUMMARY

It is the object of the present invention to eliminate the disadvantages from prior art or at least alleviate them. Preferentially, the implementation of a switchable ratchet unit in a cylindrical housing with small axial (and possibly radial) space requirement is to be presented. In addition, a means to switch a freewheel without changing the directional setting is to be provided. A directional setting from left-hand to right-hand rotation is particularly desired, even including a directly connected switching position, in this or another order. The interposition of the state of direct connection between the left-hand and right-hand rotation from the one or other side is also desirable.

This object is achieved by a ratchet as described herein.

The toothed unit comprises two torque transfer sleeves (axially telescoped torque transfer sleeves) which are arranged in a nested manner and arranged and designed such that both of them can be brought into a preferably frontal on the face side, torque-transmitting contact (teeth meshing engagement) with an (axially spaced) intermediate sleeve, such as in the manner of a disengagement shaft. The torque transfer sleeves may also be referred to as torque transfer hollow cylinder, torque transfer bushes or torque transfer rings. And the intermediate sleeve could be referred to as an intermediate hollow cylinder, intermediate bushing or intermediate ring. If the two torque transfer sleeves are axially shafted, it is possible to selectively bring one of the torque transfer sleeves into a torque transfer engagement with the intermediate sleeve. If the two torque transfer sleeves are equipped with engagement teeth each acting in different rotary directions and slipping in opposite rotary directions, a ratchet function with the possibility of selecting the sense of rotation is obtained.

In one ratchet for a medical device (the ratchet is installed in/on the medical device), the ratchet includes the previously mentioned torque-guiding element and torque discharging element between which a switchable toothed unit (ratchet gearing) is arranged such that depending on a switching position of the toothed unit a torque is transferred from the torque-guiding element to the torque discharging element. According to the invention, the toothed unit comprises the two torque transfer sleeves (arranged in a nested manner) which are mounted one inside the other and arranged and produced such that both can be brought into torque-transmitting contact with an (axially spaced) intermediate sleeve.

Specifically, a ratchet of a medical device is proposed which has a torque-guiding element (e.g. ratchet housing) that is arranged so as to be rotatable relatively around/with respect to a torque-discharging element (e.g. an output shaft preferably supported in the housing) and, for torque transfer, is coupled to it via a toothed unit winch defines a freewheel that can be switched with selectable sense of rotation, said toothed unit comprising a first torque transfer sleeve which is coupled to/in the torque-guiding element in a non-rotatable and axially fixed manner and a second torque transfer sleeve which is coupled to in the torque-guiding element so as to be rotationally fixed therewith but axially movable, which comprise toothings (toothing means) that act in opposite directions, and which depending on a manually adjustable axial position of the second torque transfer sleeve can be selectively but alternately brought into a (direct/indirect) meshing engagement with an intermediate sleeve which is arranged so as to be axially movable and preloaded toward the toothings of the torque transfer sleeve coupled to the torque-discharging element coupled for torque transfer.

The ratchet is preferably characterized in that the first torque transfer sleeve and the second torque transfer sleeve are arranged so as to be radially superimposed.

More preferably, the ratchet is characterized by an operating element or slide by means of which the manually adjustable axial position of the second torque transfer sleeve can be switched to a first position in which the second torque transfer sleeve is disengaged from the intermediate sleeve and the intermediate sleeve is in engagement with the first torque transfer sleeve due to the preload, and to a second position in which the second torque transfer sleeve is in engagement with the intermediate sleeve and shifts the latter against the preload out of engagement with the first torque transfer sleeve.

More preferably, the ratchet is characterized in that one of the two torque transfer sleeves is formed in the manner of a first detent shaft and the other torque transfer sleeve is formed in the manner of a second detent shaft and/or the intermediate sleeve is arranged to be axially movable relative to a guide shaft, said guide shaft being arranged to be axially movable relative to the torque discharging element in order to realize the freewheel.

More preferably, the ratchet is characterized in that the torque-guiding element is formed as a housing in which the two torque sleeves are accommodated and the torque-discharging element preferably forms an output shaft which is surrounded by the housing.

More preferably, the ratchet is characterized in that the one torque transfer sleeve and the other torque transfer sleeve have their respective toothing provided in axial alignment on a respective end face.

More preferably, the ratchet is characterized in that the toothings (on the torque transfer sleeves) are formed in each case as a saw toothing.

More preferably, the ratchet is characterized in that the toothings differ from each other (have different orientations relative to each other).

More preferably, the ratchet is characterized in that the toothing of the first detent shaft is provided radially inside or outside the toothing of the second detent shaft.

The above, possibly optional features allow to achieve the following effects:

It is of advantage if one of the two torque transfer sleeves is formed in the manner of a first detent shaft and the other torque transfer sleeve in the manner of a second detent shaft. This reduces the radial space requirement.

It is also advantageous if the intermediate sleeve is arranged to be axially movable relative to a guide shaft and the guide shaft is arranged to be axially movable relative to the torque discharging element to implement a freewheel. This allows a long-term operation without wear.

In order to provide for good switching ability, it is advantageous if the first detent shaft is attached to the torque-guiding element in non-rotatable manner and in axially fixed fashion.

In this respect, it is also beneficial if the second detent shaft is attached to the torque-guiding element in non-rotatable manner but so as to be axially movable.

In order to simplify assembly and construction, it is advantageous if the torque-guiding element is formed as a housing, in particular as a cylindrical housing in which the two torque sleeves are preferably completely housed/accommodated.

If one torque transfer sleeve and/or the other torque transfer sleeve comprises a toothing at an end face, it is possible to achieve an effectual torque transfer between the individual components while having short axial switching paths.

In order to enable slipping in the one direction but allow a torque transfer in the other direction, it is advantageous if the toothing is formed as a saw toothing. The principle of a ratchet, i.e. the transmission of torque in the one direction and the slipping in the other direction, such as in the manner of an overrunning coupling or a freewheel, can be effectually reproduced.

An advantageous exemplary embodiment is also characterized in that the toothings are designed so as to differ from each other, i.e. preferably realized in opposite and/or inverse design. It is expedient if the toothing of at least one of the torque transfer sleeves is designed/arranged/shaped to be annular.

For allowing a selective switching process, it is advantageous if the intermediate sleeve is arranged to be axially movable.

In order to provide an efficient torque transfer, it is advantageous if the intermediate sleeve is connected to the torque discharging element in non-rotatable manner, such as by interposing one or more intermediate parts.

A high efficiency and a safe functioning during right and left hand rotation as well as with a fixed connection in both directions is ensured if the end face of the intermediate sleeve has/comprises a complementary soothing which is sized and prepared for receiving the toothing of both torque transfer sleeves.

In this context, it is advantageous if the complementary toothing formed as a spur toothing. It goes without saying that claw-coupling type designs are possible as well.

An advantageous exemplary embodiment is also characterized in that the second detent shaft is firmly connected, to an e.g. pin-like operating element which projects through the torque-guiding element towards outside for moving the second detent shaft, for instance by penetrating the housing through an elongated hole.

In order to efficiently use the installation space, it is advantageous if the height of the complementary toothing as measured in radial direction corresponds to the sum of the two toothings of the torque transfer sleeves, +/−5% to 10%.

A variant is also characterized in that the second detent shaft is under spring preload in axial direction by a spring means, for example by supporting the spring means on the first detent shaft and/or the torque-guiding element, such as the housing, and the second detent shaft.

It has also proved to be successful if the spring means is formed as a compression spring, for instance a helical compression spring.

Conventional ways of coupling can be realized if the torque discharging element is formed as an output shaft.

In this context, it is advantageous if a transmission member is arranged between the output shaft and the intermediate sleeve. A modular construction can thus be achieved in an easier way.

For preventing an unnecessarily large weight, i.e. for obtaining a ratchet winch is as light-weight as possible, it is advantageous if the transmission member is formed as a hollow guide shaft. A hollow cylindrical cross-section is particularly suitable.

An interleaving in a nested manner is also suitable, for instance in such a way that the hollow guide shaft is surrounded by a tube at least in parts.

Here, it is advantageous if the intermediate sleeve is attached to the tube in a non-rotatable manner or is formed in one piece with it.

It is also possible that the detent shaft/torque transfer sleeve, which is attached to the torque-guiding element in a non-rotatable and axially fixed fashion, is formed in one piece with the housing. As an alternative, the first detent shaft can also be screwed into the housing. This simplifies production and assembly.

It is also of advantage if the tube is axially preloaded by a spring device, for instance in a direction away from the intermediate sleeve and towards the first detent shaft.

Finally, the invention also relates to a medical device comprising a ratchet of the type according to the invention.

In other words, the function is achieved substantially by three axially toothed shafts that are provided in a housing. An axially shiftable, spring-mounted disengagement shaft without directionally dependent toothing is guided on a guide shaft. The disengagement shaft may be in engagement with two different detent shafts. A detent shaft including a saw-tooth profile is rotatorily fixed to the housing and cannot be shifted. The second detent shaft is fixed rotatably in the housing, but is axially shiftable and spring-mounted and in addition has an opposite saw-tooth profile.

Both detent shafts are disposed one inside the other and hence have a space-saving design in axial as well as in radial direction. The saw-tooth profile of the shiftable detent shaft can be pushed in front of, in overlap position and behind the saw-tooth profile of the fixed detent shaft. This can be realized with three switching positions, e.g. of an operating element. A spring may serve for returning the shiftable detent shaft.

The toothing of the disengagement shaft is pushed forward the detent shall by springs. Depending on the positions of the shiftable detent shaft, a right or left-hand rotation or a force transmission in both directions (direct connection) is ensured.

As an option, the guide shaft may be guided on an output shaft which transmits the torque to a tool or the like. If the guide shaft is axially pushed away from the detent shaft, it entrains the disengagement shaft so that it comes out of contact with the detent shafts. This creates a freewheel without wear. In this freewheel mode, the guide shaft can be driven by motor power, for instance.

Up to now, telescoped toothings for saving installation space are not known in this field. A shaft which is springs-mounted in axial direction and fulfils the actual ratchet function has not been invented either so far. The implementation of a freewheel without adaptation to the switching position (left-hand and right-hand rotation fixed) is new. Moreover, the switching position can be conveniently manipulated with one operating element.

The advantages include: small axial installation space, small radial installation space, only three toothings that have to be manufactured, an easy adjustability by one operating element, a simple implementation of a freewheel, very low operating forces and a uniform transmission of the forces by an all-round toothing.

Such a ratchet can be used in the distal region of a screw driver add-on part. Due to the freewheel it is possible here to connect an electrical drive and a manual drive. This means that the utilization of the axial and radial installation space is improved. Due to the presented nested way of construction, these demands can be fulfilled in an installation-friendly way. Further, the handling is more comfortable and it is possible to use a freewheel.

BRIEF DESCRIPTION OF THE DRAWING FIGURES

Figure 1:
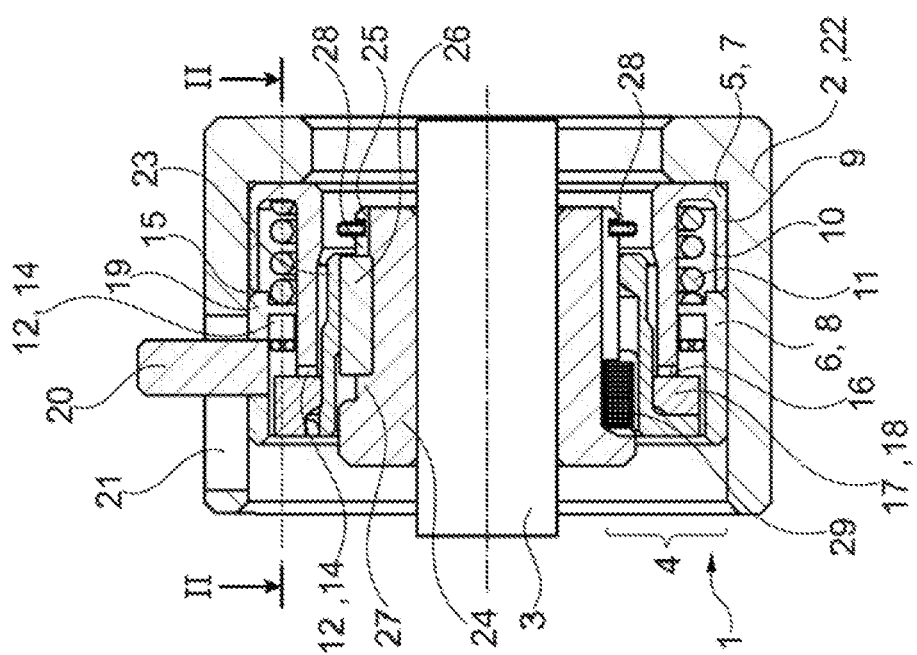
Figure 5:
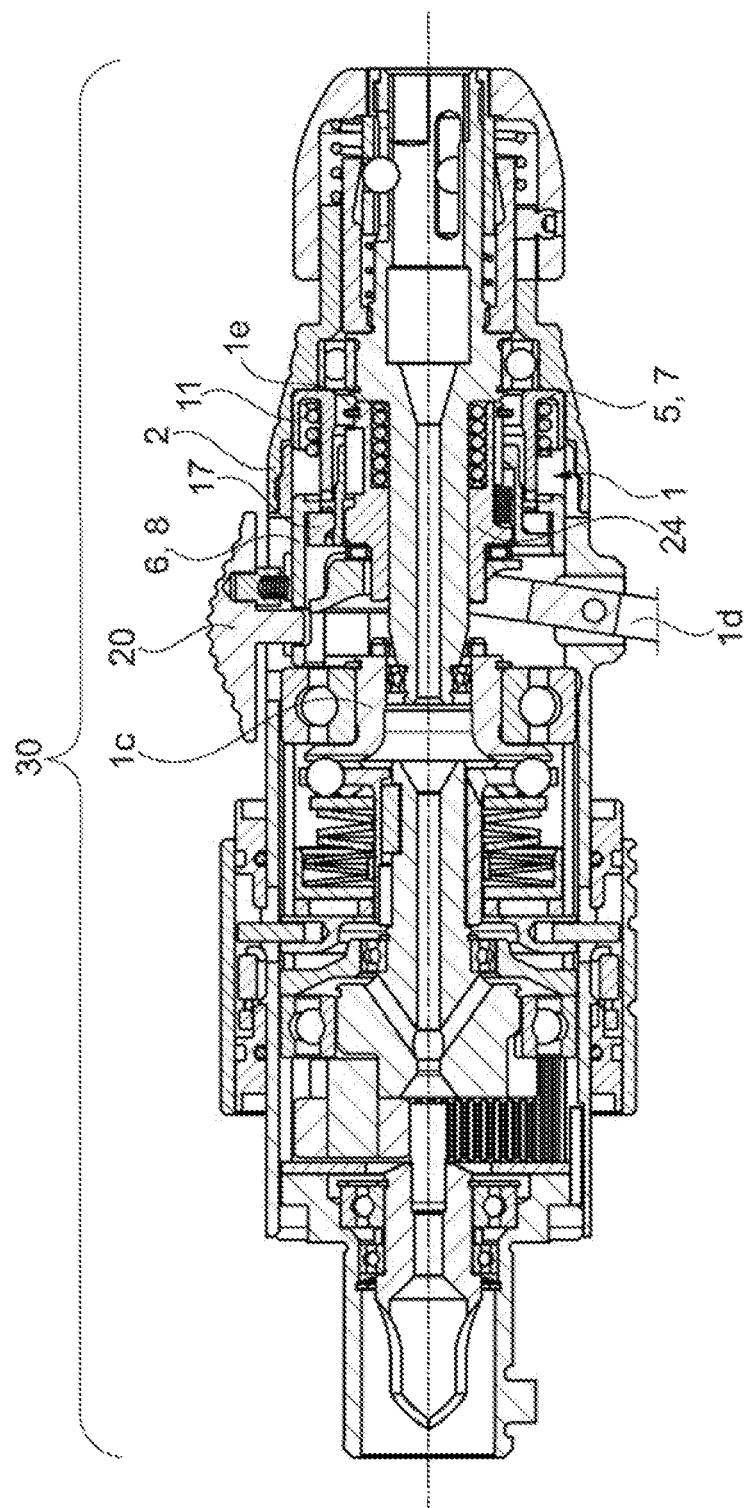

The invention will be explained below on the basis of a first exemplary embodiment of a ratchet, and the implementation in a medical device, which are shown in the attached drawings, of which:

FIG. 1 is a longitudinal section through a ratchet according to a first embodiment in a first switching position (right-hand rotation), FIG. 2 is a longitudinal section at the level of line II through the ratchet of FIG. 1, FIG. 3 is a longitudinal section through the ratchet of the first embodiment in a third switching position (left-hand rotation) which is reached after a second switching position (first-time connection), FIG. 4 is a longitudinal section along line IV of FIG. 3, and FIG. 5 is a longitudinal section through a medical device in which the ratchet is inserted in a second embodiment modified with respect to FIGS. 1 to 4.

The Figures are of schematic nature only and serve for helping to understand the detailed description. Identical elements are designated with the same reference numerals.

DETAILED DESCRIPTION

FIG. illustrates a ratchet 1 according to one embodiment. Said ratchet 1, which may also be referred to as a ratchet means or ratchet device, is in a switching position 1 in order to ensure a right-hand rotation. It has a torque-guiding or input element (input sleeve/ratchet housing) 2 and a torque discharging or output element (output sleeve/output shaft) 3. A toothed unit (ratchet gearing) 4 is provided between said two members 2 and 3. Preferably, the toothed unit 4 can be switched in manual fashion. Depending on the switching position of the toothed unit 4, a torque is transferred or can be transferred from the torque-guiding element 2 to the torque discharging element 3 in the sense of rotation selected corresponding to the switching position. Depending on the switching position and the sense of rotation on the torque-guiding element 2, the torque is transferred to the torque discharging element 3 or not.

The toothed unit 4 comprises two (axially telescoped) torque transfer sleeves 5 and 6 arranged in a nested manner. This means that one of the in is arranged so as to be situated further outside or inside than the other one and preferably concentrically to it.

The first torque transfer sleeve 5 is formed in the manner of a first detent shaft 7, whereas the second torque transfer sleeve 6 is formed in the manner of a second detent shaft 8. The two detent shafts 7 and 8 have a preferably bushing-type or pot-like design and comprise in this preferred case flanges pointing outwards or inwards. An external flanging 9 of the first detent shaft 7 defines an annular cavity 10 in which a spring means 11 is arranged. In any operational state, the spring means 11 is in abutment on the second detent shaft 8 and the first detent shaft 7. Generally speaking, the two detent shafts 7, 8 or torque transfer sleeves 5, 6 are axially preloaded by the spring means 11 with respect to each other (away from each other).

The two detent shafts 7 and 8 comprise toothings 12 on the same end face. The toothing 12 of the first detent shaft 7 is formed on a frontal end 13 of the first detent shaft 7. This toothing 12 is formed as a saw toothing 14. A web 15 radially protruding inward from an outer wall of the second detent shaft 8 has its frontal face likewise provided with a toothing 12 which is designed as a saw toothing 14 as well. The two saw toothings 14, however, have an opposite configuration. The one saw toothing 14 is formed as a left-hand toothing, whereas the other saw toothing 14 is formed as a right-hand toothing.

The two saw toothings 14 can be made to engage a complementary toothing 16 provided on an intermediate sleeve 17 which is designed in the manner of a disengagement shaft 18. The disengagement shaft 18 also has an end face 19 on which the complementary toothing 16 is formed. The complementary toothing 16 is not realized as a saw toothing, but in the form of a spur toothing or claw coupling type toothing.

An operating element 20 extends through an elongated hole 21 in the torque-guiding element 2 formed as a housing 22 and is fixed in the second torque transfer sleeve 6 or in engagement therein.

A tube 23 is connected to the intermediate sleeve 17 in a torque-proof manner and possibly in axially fixed fashion. The two components may also be formed in one piece. Provided radially inside the tube 23 is a guide shaft 24 which comprises an outer toothing, allowing the transfer of a torque, or at least one groove 25 into which a pin/feather key 26 is inserted. In axial direction, the pin 26 is arranged between a shoulder 27 of the guide shaft 24 and a snap ring 28.

A spring device 29 is inserted for imposing an axial preload of the tube 23 relative to the guide shaft 24.

FIG. 2 shows the radially inner toothing 12 of the first torque transfer sleeve 5 (i.e. the first detent shaft 7) relative to the second torque transfer sleeve 6 (i.e., the second detent shaft 8) with its toothing 12. The saw toothing 14 of the first detent shaft 7 is in engagement with the directionally independent complementary toothing 16 of the intermediate sleeve 17.

FIGS. 3 and 4 illustrate a process of switching to left-hand rotation, and it can be seen that the saw toothing 14 of the second detent shall 8 is in torque-transmitting engagement with the complementary toothing 16 of the intermediate sleeve 17 and the intermediate sleeve 17 is axially displaced and exactly not in engagement with the saw toothing 14 of the first torque transfer sleeve 5/first detent shaft 7.

The spring means 11 as well as the spring device 29 is a helical compression spring.

FIG. 5 illustrates a medical device 30 with a modified ratchet 1.

Thus, the ratchet 1 according to FIG. 3 consists of the housing 2 (torque-guiding element) as a manual drive unit, in which the two sleeve-shaped torque transfer elements (torque transfer sleeves) 5, 6 are received in the housing 2 in a torque-proof manner, of which at least one torque transfer element 6 is held to be axially movable with respect to the other torque transfer element 5. Both torque transfer elements (torque transfer sleeves) 5, 6 preferably have their end face equipped with the above-mentioned toothings 12 in order to be brought—alternately and selectively depending on their axial mutual relative position—in meshing engagement with the intermediate sleeve or an intermediate/selection component 17 preferably in the form of a disc or ring axially adjoining the torque transfer elements and in this way transmit a torque in clockwise or anticlockwise direction to the intermediate sleeve 17.

The relative axial position of the two torque transfer sleeves 5, 6 can be adjusted by means of the manually operable slide/operating element 20. The slide 20 is coupled to one of the two torque transfer elements 5, 6 in order to shift a in axial direction. This has the effect that the at least one axially shiftable torque transfer element comes into meshing engagement with the intermediate/selection component 17 or is disengaged therefrom. The intermediate/selection component 17 is also held to be axially shiftable and is biased by a spring toward the two torque transfer elements 5, 6. If the one torque transfer element 6 is axially pressed by means of the slide 20 against the intermediate selection component 17 to come in meshing engagement with the latter, said intermediate/selection component 17 is continued to be axially shifted against the spring preload whereby the meshing engagement with the other torque transfer element 5 is removed and vice versa.

As already explained above, the toothings of the two torque transfer elements 5, 6 work in opposite directions such that they can transmit a right-hand or left-hand torque only and act as a freewheel in the other direction. Depending, on the selected torque transfer element, only a right-sense or left-sense torque can be transmitted from the manual drive unit (housing 2) via the ratchet/the ratchet gearing. Furthermore, the intermediate/selection component 17 is supported by the guide sleeve (sleeve-shaped ratchet output element 24) so as so be axially shiftable but rotationally fixed therewith, which in turn is supported by the shaft of the output-side coupling 3 so as to be rotationally fixed therewith but axially shiftable.

The end face of the ratchet output element 24 is preferably provided with a toothing by means of which the ratchet output element 24, depending on its axial position with aspect to the shaft of the output-side coupling 3, can come into a torque-transmitting meshing engagement with an output element 1c of the input-side coupling in order to transfer a torque from the motor to the output-side of the coupling.

The manual drive unit (housing) 2 is activated and driven by a lever 1d. To this end, the lever 1d is formed in the manner of a crank and adapted to the size of a human hand. In other words, the lever 1d is journaled in the housing 2 in such a manner that the housing 2 can be rotated using the lever 1d around the center axis of the tool mount and the torque transfer elements 5, 6 can be driven. However, the lever 1d is also pivotally mounted in axial direction of the tool mount, as shown in FIG. 5. A lever protrusion projecting into the housing interior is coupled to the ratchet output element 24 such that the latter can be shifted by pivoting the lever 1d in axial direction.

The ratchet output element 24 has a dog in the form of the radial protrusion or shaft ring 28 which acts on the intermediate/selection component 17 of the ratchet in direct or indirect manner for possibly entraining it in accordance with the axial movement of the ratchet output element (guide sleeve) 24.

If the ratchet output element 24 is moved via the lever 1d axially against the output element 1c of the input-side coupling into a torque-transmitting meshing engagement, the intermediate/selection component 17 of the ratchet is entrained to an axial position in which it cannot come into meshing engagement with one of the two torque transfer elements 5, 6 any more. In this case, a torque is indeed transferred from the motor to the output-side coupling 3, but the ratchet function is nullified. On the contrary, if the ratchet output element 24 is shifted axially away from the output element 1c of the input-side coupling (no meshing engagement) via the lever 1d, the intermediate/selection component 17 of the ratchet is entrained/urged to an axial position in which it can come into meshing engagement with one of the two torque transfer elements 5, 6. In this case, it is not possible to transmit any torque from the motor to the output-side coupling 3, but the ratchet function is put into effect to transmit a torque manually introduced on the lever 1d. This results in a decoupler, so to speak.

The invention claimed is:

1. A ratchet of a medical device comprising: a torque-guiding/-input element which is arranged so as to be rotatable around/with respect to a torque-discharging/-output element and, for torque transfer, is coupled to the torque-discharging/-output element via a toothed unit or transmission which forms a freewheel with selectable sense of rotation and has a first torque transfer sleeve which is coupled to/in the torque-guiding/-input element in a non-rotatable and axially fixed manner and a second torque transfer sleeve which is coupled to/in the torque-guiding/-input element so as to be rotationally fixed with but axially movable relative to the torque-guiding/-input element, the first torque transfer sleeve comprising a first toothing and the second torque transfer sleeve comprising a second toothing that acts in an opposite direction of the first toothing, and depending on a manually adjustable axial position of the second torque transfer sleeve, the first and second toothings can be selectively but alternately brought into meshing engagement with an intermediate sleeve which is arranged so as to be axially movable relative to the first and second toothings, is preloaded toward the first and second toothings of the first and second torque transfer sleeves, and is coupled to the torque-discharging/-output element for torque transfer.

2. The ratchet according to claim 1, wherein the first torque transfer sleeve and the second torque transfer sleeve are arranged so as to be radially superimposed.

3. The ratchet according to claim 2, comprising an operating element by which the manually adjustable axial position of the second torque transfer sleeve can be switched to a first position in which the second torque transfer sleeve is disengaged from the intermediate sleeve and the intermediate sleeve is in engagement with the first torque transfer sleeve due to a preload, and to a second position in which the second torque transfer sleeve is in engagement with the intermediate sleeve and shifts the intermediate sleeve against the preload out of engagement with the first torque transfer sleeve.

4. The ratchet according to claim 1, wherein the first torque transfer sleeve is formed as a first detent shaft and the second torque transfer sleeve is formed as a second detent shaft and/or the intermediate sleeve is arranged to be axially movable relative to a guide shaft, said guide shaft being arranged to be axially movable relative to the torque discharging/output-element in order to realize the freewheel.

5. The ratchet according to claim 4, wherein the first toothing of the first detent shaft is provided radially inside or outside the second toothing of the second detent shaft.

6. The ratchet according to claim 1, wherein the torque-guiding/input-element is formed as a housing in which the first and second torque transfer sleeves are accommodated, and the torque-discharging/output-element forms an output shaft which is surrounded by the housing.

7. The ratchet according to claim 1, wherein the first and second torque transfer sleeves have their respective first and second toothings provided in axial alignment on a respective end face.

8. The ratchet according to claim 7, wherein the first and second toothings are formed in each case as a saw toothing.

9. The ratchet according to claim 7, wherein the first and second toothings differ from each other.

10. A medical device comprising a ratchet according to claim 1.

11. The medical device according to claim 10, wherein the medical device comprises a medical drilling/screwing machine.

* * * * *